United States Patent
Audousset

[11] Patent Number: 5,900,028
[45] Date of Patent: May 4, 1999

[54] OXIDATION DYE COMPOSITION FOR KERATIN FIBRES COMPRISING 2-AMINO-3-HYDROXYPYRIDINE AND A P-PHENYLENEDIAMINE OR P-AMINOPHENOL OXIDATION BASE, AND DYEING PROCESS

[75] Inventor: Marie-Pascale Audousset, Asnieres, France

[73] Assignee: L'Oreal, Paris, France

[21] Appl. No.: 08/725,257

[22] Filed: Oct. 4, 1996

[30] Foreign Application Priority Data

Oct. 6, 1995 [FR] France .................... 95 11808

[51] Int. Cl.⁶ ........................... A61K 7/13
[52] U.S. Cl. .............. 8/409; 8/410; 8/412; 8/416; 8/421; 8/423; 8/568
[58] Field of Search ................ 8/409, 410, 411, 8/416, 421, 423, 568, 649

[56] References Cited

U.S. PATENT DOCUMENTS

| | | | |
|---|---|---|---|
| 3,884,627 | 5/1975 | Brody et al. | 8/410 |
| 3,970,423 | 7/1976 | Brody et al. | 8/410 |
| 4,165,967 | 8/1979 | Bühler et al. | 8/429 |
| 5,421,833 | 6/1995 | Lorenz | 8/409 |
| 5,494,489 | 2/1996 | Akram et al. | 8/409 |

FOREIGN PATENT DOCUMENTS

| | | |
|---|---|---|
| 0 559 217 | 3/1993 | European Pat. Off. . |
| 1398193 | 4/1964 | France . |
| 2156527 | 4/1972 | France . |
| 2714831 | 4/1977 | Germany . |
| 2739227 | 8/1977 | Germany . |
| 3009833 | 3/1980 | Germany . |
| 2180215 | 9/1986 | United Kingdom . |
| WO94/27564 | 5/1994 | WIPO . |

*Primary Examiner*—Paul Liberman
*Assistant Examiner*—Caroline L. Dusheck
*Attorney, Agent, or Firm*—Finnegan, Henderson, Farabow, Garrett & Dunner, L.L.P.

[57] ABSTRACT

An oxidation dye composition for keratin fibre, in particular human hair, comprising at least one 2-amino-3-hydroxypyridine as coupler, in combination with at least one suitably selected oxidation base, as well as the dyeing process using this composition with an oxidizing agent.

23 Claims, No Drawings

OXIDATION DYE COMPOSITION FOR KERATIN FIBRES COMPRISING 2-AMINO-3-HYDROXYPYRIDINE AND A P-PHENYLENEDIAMINE OR P-AMINOPHENOL OXIDATION BASE, AND DYEING PROCESS

The present invention relates to an oxidation dye composition for keratin fibres, in particular human keratin fibres such as the hair, comprising at least one coupler selected from 2-amino-3-hydroxypyridine and acid addition salts thereof, in combination with at least one suitably selected oxidation base, as well as to the dyeing process using this composition with an oxidizing agent.

It is known to dye keratin fibres, and in particular human hair, with dye compositions containing oxidation dye precursors, in particular ortho or paraphenylenediamines, ortho- or para-aminophenols, or heterocyclic compounds such as pyrimidine derivatives, which are generally referred to as oxidation bases. The oxidation dye precursors, or oxidation bases, are colourless or weakly coloured compounds which, when combined with oxidizing products, may give rise to coloured compounds and dyes by a process of oxidative condensation.

It is also known that the shades obtained with oxidation bases may be varied by combining them with suitably selected couplers or coloration modifiers, it being possible for the latter to be chosen in particular from aromatic meta-diamines, meta-aminophenols, meta-diphenols and certain heterocyclic compounds such as pyridine derivatives.

The variety of molecules used as oxidation bases and couplers makes it possible to obtain a wide range of colours.

The so-called "permanent" coloration obtained by means of these oxidation dyes must satisfy a certain number of requirements. For example, it must have no toxicological drawbacks and it must allow shades of the desired intensity to be obtained and have good resistance to external agents (light, inclement weather, washing, permanent-waving, perspiration and rubbing).

The dyes must also allow white hairs to be covered and, lastly, they must be as unselective as possible, that is to say that they must allow the smallest possible differences in coloration to be produced over the entire length of the same keratin fibre, which may indeed be differently sensitized (for example if damaged) between its tip and its root.

The term "selectivity" also applies to a group of fibres, for example, a head of hair. In other words, the term "selectivity" describes a lack of consistency in color of a dye on an entire head of hair. Dyes must be as unselective as possible on the whole head of hair. That is to say that they must allow the smallest possible differences in coloration to be produced over the entire head of hair, which may include single fibres that are differently sensitized.

Compositions for the oxidation dyeing of keratin fibres containing 2-amino-3-hydroxypyridine as coupler, in combination with heterocyclic oxidation bases, in particular 2,4,5,6-tetraaminopyrimidine or with diazo compounds such as N-phenylaminoaniline, have already been proposed, in particular in German patent applications DE 2,714,831 and DE 2,739,227.

However, such compositions are not entirely satisfactory, in particular from the point of view of the resistance of the colorations obtained to the various attacking factors to which the hair may be subjected and, in particular, to shampoos.

Now, the inventor has surprisingly discovered that it is possible to obtain novel dyes by combining at least one coupler selected from 2-amino-3-hydroxypyridine and acid addition salts thereof and at least one suitably selected oxidation base, these dyes being relatively unselective, particularly resistant, and capable of giving rise to intense colorations in varied shades.

This discovery forms the basis of the present invention.

The subject of the invention is thus a composition for the oxidation dyeing of keratin fibres, and in particular human keratin fibres such as the hair, characterized in that it comprises, in a medium which is suitable for dyeing:

at least one coupler selected from 2-amino-3-hydroxypyridine and acid addition salts thereof, and at least one oxidation base selected from:

(a) para-phenylenediamine derivatives of formula (I), and acid addition salts thereof:

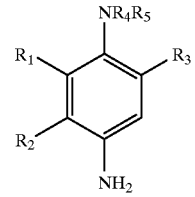

(I)

wherein:
$R_1$, $R_2$ and $R_3$ are independently selected from hydrogen, halogen, $C_1$–$C_4$ alkyl, $C_1$–$C_4$ alkoxy, sulpho, carboxyl, $C_1$–$C_4$ monohydroxyalkyl and $C_2$–$C_4$ polyhydroxyalkyl radicals;
$R_4$ and $R_5$ are independently selected from hydrogen, $C_1$–$C_4$ alkyl, $C_1$–$C_4$ monohydroxyalkyl, $C_2$–$C_4$ polyhydroxyalkyl, ($C_1$–$C_4$)alkoxy($C_1$–$C_4$)alkyl, carbamyl($C_1$–$C_4$) alkyl, mesylamino-($C_1$–$C_4$)alkyl, acetylamino ($C_1$–$C_4$)alkyl, ureido($C_1$–$C_4$)alkyl, carb($C_1$–$C_4$) alkoxyamino($C_1$–$C_4$)alkyl, $C_1$–$C_4$ sulphoalkyl, piperidino($C_1$–$C_4$)alkyl and morpholino($C_1$–$C_4$) alkyl radicals; or alternatively $R_4$ and $R_5$ form, together with the nitrogen atom to which they are attached, a heterocycle selected from a piperidino heterocycle and a morpholino heterocycle;

and further wherein:
at least one of the radicals $R_1$, $R_2$, $R_3$, $R_4$ and $R_5$ is not a hydrogen atom,
when the radicals $R_4$ and $R_5$ simultaneously represent a hydrogen atom and when two of the radicals $R_1$, $R_2$ and $R_3$ simultaneously denote a hydrogen atom, then the remaining radical $R_1$, $R_2$ or $R_3$ that is not a hydrogen atom, is also not a methyl radical,
when $R_4$ and $R_5$ do not simultaneously represent a hydrogen atom, then at least one of the radicals $R_1$, $R_2$ and $R_3$ must represent a hydrogen atom; and (b) para-aminophenols and acid addition salts thereof.

The oxidation dye composition in accordance with the invention makes it possible to obtain colorations in varied shades, which are relatively unselective and have excellent properties of resistance both to atmospheric agents such as light and inclement weather and to perspiration and the various treatments to which the hair may be subjected (e.g. shampooing and permanent-waving). These properties are particularly noteworthy, especially as regards the resistance of the colorations to shampooing.

Among the $C_1$–$C_4$ alkyl and $C_1$–$C_4$ alkoxy radicals of formula (I) above, mention may be made in particular of the methyl, ethyl, propyl, methyloxy and ethyloxy radicals.

Among the para-phenylenediamine derivatives of formula (I) above, which can be used as oxidation base in the dye compositions in accordance with the invention, mention may be made more particularly of 2-chloro-para-phenylenediamine, 2,3-dimethyl-para-phenylenediamine, 2,6-dimethyl-para-phenylenediamine, 2,6-diethyl -para-phenylenediamine, 2,5-dimethyl-para-phenylenediamine, 2-methyl-5-methoxy-para-phenylenediamine, 2,6-dimethyl-5-methoxy-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-amino-N,N-bis(β-hydroxyethyl)-3-methylaniline, 4-amino-3-chloro-N,N-bis(β-hydroxyethyl) aniline, 4-amino-N-ethyl-N-carbamylmethyl-aniline, 4-amino-3-methyl-N-ethyl-N-carbamylmethyl-aniline, 4-amino-N-ethyl-N-(β-piperidinoethyl)aniline, 4-amino-3-methyl-N-ethyl-N-(β-piperidinoethyl)aniline, 4-amino-N-ethyl-N-(β-morpholinoethyl)aniline, 4-amino-3-methyl-N-ethyl-N-(β-morpholinoethyl)aniline, 4-amino-ethyl-N-(β-acetylaminoethyl)aniline, 4-amino-N-(β-methoxyethyl) aniline, 4-amino-3-methyl-N-ethyl-N-(β-acetylaminoethyl) aniline, 4-amino-N-ethyl-N-(β-mesylaminoethyl)aniline, 4-amino-3-methyl-N-ethyl-N-(β-mesylaminoethyl)aniline, 4-amino-N-ethyl-N-(β-sulphoethyl)aniline, 4-amino-3-methyl-N-ethyl-N-(β-sulphoethyl)aniline, N-[4'-(amino) phenyl]morpholine, N[4'-(amino)phenyl]piperidine, 2-β-hydroxyethyl-para-phenylenediamine, 2-fluoro-para-phenylenediamine, 2-carboxy-para-phenylenediamine, 2-sulpho-para-phenylenediamine, 2-isopropyl-para-phenylenediamine, N-(βhydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, and 2-β-hydroxyethyloxy-para-phenylenediamine, and acid addition salts thereof.

Among the para-aminophenols which can be used as oxidation bases in the context of the compositions in accordance with the invention, mention may be made in particular of the compounds corresponding to formula (II) below, and the acid addition salts thereof:

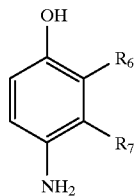

(II)

wherein:
$R_6$ is selected from hydrogen, $C_1$–$C_4$ alkyl, $C_1$–$C_4$ monohydroxyalkyl, $(C_1$–$C_4)$alkoxy$(C_1$–$C_4)$alkyl, $C_1$–$C_4$ aminoalkyl, and hydroxy$(C_1$–$C_4)$alkylamino $(C_1$–$C_4)$alkyl;
$R_7$ is selected from hydrogen, fluorine, $C_1$–$C_4$ alkyl, $C_1$–$C_4$ monohydroxyalkyl, $C_2$-$C_4$ polyhydroxyalkyl, $C_1$–$C_4$ aminoalkyl, cyano$(C_1$–$C_4)$alkyl, and $(C_1$–$C_4)$ alkoxy$(C_1$–$C_4)$alkyl;
and further wherein at least one of the radicals $R_6$ and $R_7$ represents a hydrogen atom.

Among the para-aminophenols of formula (II) above, mention may be made more particularly of para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol and 4-amino-2-(β-hydroxyethylaminomethyl)phenol, and acid addition salts thereof.

The acid addition salts which can be used in the context of the dye compositions of the invention (2-amino-3-hydroxypyridine and oxidation bases) are preferably chosen from hydrochlorides, hydrobromides, sulphates and tartrates.

The at least one coupler, i.e., the 2-amino-3-hydroxypyridine and the at least one acid addition salt thereof preferably represent approximately from 0.0001 to 5% by weight relative to the total weight of the dye composition, and even more preferably approximately from 0.005 to 3% by weight relative to this weight.

The at least one oxidation base selected from para-phenylenediamine derivatives of formula (I) and para-aminophenols of formula (II) and acid addition salts thereof preferably represent approximately from 0.0005 to 12% by weight relative to the total weight of the dye composition, and even more preferably approximately from 0.005 to 6% by weight relative to the total weight of the dye composition.

The dye compositions in accordance with the invention may contain other couplers different from 2-amino-3-hydroxypyridine and/or other oxidation bases different from the para-phenylenediamine derivatives of formula (I) and para-aminophenols of formula (II) and/or direct dyes, in particular in order to modify the shades or to enrich them with glints.

The appropriate medium (or the support) for the dyeing generally comprises water or a mixture of water and at least one organic solvent to solubilize the compounds which would not be sufficiently soluble in water.

Organic solvents which may be mentioned, for example, are $C_1$–$C_4$ lower alkanols such as ethanol and isopropanol; glycerol; glycols and glycol ethers such as 2-butoxyethanol, propylene glycol, propylene glycol monomethyl ether, diethylene glycol monoethyl ether and monomethyl ether, and aromatic alcohols such as benzyl alcohol or phenoxyethanol, similar products and mixtures thereof.

The solvents may be present in proportions preferably ranging approximately from 1 to 40% by weight relative to the total weight of the dye composition, and even more preferably ranging approximately from 5 to 30% by weight relative to the total weight of the dye composition.

The pH of the dye composition in accordance with the invention preferably ranges from approximately 3 to 12 and even more preferably from approximately 5 to 11. The pH of the dye composition in accordance with the invention may be adjusted to the desired value using acidifying or basifying agents commonly used in the dyeing of keratin fibres.

Among the acidifying agents which may be mentioned, by way of example, are inorganic or organic acids such as hydrochloric acid, orthophosphoric acid, carboxylic acids such as tartaric acid, citric acid and lactic acid, and sulphonic acids.

Among the basifying agents which may be mentioned, by way of example, are aqueous ammonia, alkaline carbonates, alkanolamines such as mono-, di- and triethanolamines and derivatives thereof, sodium hydroxide, potassium hydroxide and the compounds of formula (III) below:

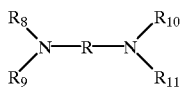

(III)

wherein:

R is a propylene residue optionally substituted with a hydroxyl group or a $C_1$–$C_4$ alkyl radical;

$R_8$, $R_9$, $R_{10}$ and $R_{11}$ are independently selected from hydrogen, a $C_1$–$C_4$ alkyl and $C_1$–$C_4$ hydroxyalkyl radical.

The dye composition according to the invention may also include various adjuvants used conventionally in compositions for dyeing the hair, such as anionic, cationic, nonionic, amphoteric or zwitterionic surfactants or mixtures thereof, anionic, cationic, nonionic, amphoteric or zwitterionic polymers or mixtures thereof, inorganic or organic thickeners, antioxidants, penetration agents, sequestering agents, fragrances, buffers, dispersing agents, conditioners such as, for example, silicones, film-forming agents, preserving agents and opacifying agents.

A person skilled in the art will take care to select this or these optional complementary adjuvant(s) such that the advantageous properties intrinsically associated with the combination in accordance with the invention are not, or are substantially not, adversely affected by the addition or additions envisaged.

The dye composition according to the invention may be in various forms, such as in the form of liquids, creams, gels or any other form which is suitable for dyeing keratin fibres, and in particular human hair.

The subject of the invention is also a process for dyeing keratin fibres, and in particular human keratin fibres such as the hair, using the dye composition as defined above.

According to this process, the dye composition as defined above is applied to the fibres, the colour being developed at acidic, neutral or alkaline pH using an oxidizing agent which is added only at the time of use to the dye composition or which is present in an oxidizing composition that is applied simultaneously or sequentially in a separate manner.

According to a particularly preferred embodiment of the dyeing process according to the invention, the dye composition described above is mixed, at the time of use, with an oxidizing composition containing, in a medium which is suitable for dyeing, at least one oxidizing agent present in an amount which is sufficient to develop a coloration. The mixture obtained is then applied to the keratin fibres and is left in place for preferably 3 to 50 minutes approximately, more preferably 5 to 30 minutes approximately, after which the fibres are rinsed, washed with shampoo, rinsed again and dried.

The oxidizing agent present in the oxidizing composition as defined above may be chosen from the oxidizing agents conventionally used for the oxidation dyeing of keratin fibres, and among which mention may be made of hydrogen peroxide, urea peroxide, alkali metal bromates and persalts such as perborates and persulphates. Hydrogen peroxide is particularly preferred.

The pH of the oxidizing composition containing the oxidizing agent as defined above is such that, after mixing with the dye composition, the pH of the resulting composition applied to the keratin fibres preferably ranges approximately from 3 to 12 and even more preferably from approximately 5 to 11. It is adjusted to the desired value using acidifying or basifying agents usually used in the dyeing of keratin fibres and as are defined above.

The oxidizing composition as defined above may also include various adjuvants used conventionally in compositions for dyeing the hair and as are defined above.

The composition which is finally applied to the keratin fibres may be in various forms, such as in the form of liquids, creams, gels or any other form which is suitable for dyeing keratin fibres, and in particular human hair.

Another subject of the invention is a multi-compartment device for dyeing or dyeing "kit" or any other multi-compartment packaging system a first compartment of which contains the dye composition as defined above and a second compartment of which contains the oxidizing composition as defined above. These devices may be equipped with a means which makes it possible to deliver the desired mixture onto the hair, such as the devices described in patent FR-2,586,913, the disclosure of which is specifically incorporated by reference herein.

The examples which follow are intended to illustrate the invention without, however, limiting the scope thereof.

EXAMPLES

Comparative Examples 1 and 2

The following dye compositions were prepared (contents in grams):

| EXAMPLE | 1(*) | 2 |
|---|---|---|
| 2,4,5,6-Tetraaminopyrimidine monohydrate monosulphate | 0.238 | — |
| 2,6-Dimethyl-para-phenylenediamine dihydrochloride | | 0.209 |
| 2-Amino-3-hydroxypyridine | 0.110 | 0.110 |
| Common dye support | () | () |
| Demineralized water qs | 100 g | 100 g |

It is important to note that the dye compositions of Examples 1 and 2 contained the same molar amount of oxidation base, i.e. $1 \cdot 10^{-3}$ mol.

(*): composition not forming part of the invention (**): Common dye support:

Oleyl alcohol polyglycerolated with 2 mol of glycerol 4.0 g

Oleyl alcohol polyglycerolated with 4 mol of glycerol, containing 78% of active material (AM) 5.69 g AM Oleic acid 3.0 g Oleylamine containing 2 mol of ethylene oxide, sold under the trade name Ethomeen O12 by the company Akzo 7.0 g Diethylaminopropyl laurylamino succinimate, sodium salt, containing 55% AM 3.0 g AM Oleyl alcohol 5.0 g Oleic acid diethanolamide 12.0 g Propylene glycol 3.5 g Ethyl alcohol 7.0 g Dipropylene glycol 0.5 g Propylene glycol monomethyl ether 9.0 g Sodium metabisulphite in aqueous solution, containing 35% AM 0.455 g AM Ammonium acetate 0.8 g Antioxidant, sequestering agent qs Fragrance, preserving agent qs Aqueous ammonia containing 20% $NH_3$ 10.0 g Each dye composition was mixed, at the time of use, with an equal weight amount of 20-volumes aqueous hydrogen peroxide solution (6% by weight).

Each resulting composition had a pH of about 10 and was applied for 30 minutes to locks of natural grey hair containing 90% white hairs. The locks of hair were then rinsed, washed with a standard shampoo and then dried.

The locks of hair thus dyed were then subjected to a test of resistance to shampooing (Ahiba-Texomat machine).

To do this, the locks of dyed hair were placed in a basket which was immersed in a solution of a standard shampoo. The basket was subjected to an up-and-down motion of variable frequency as well as to a rotational motion, which reproduced the action of manual rubbing, thereby causing the formation of foam.

After a test time of 3 minutes, the locks were removed and then rinsed and dried.

The locks were subjected to 6 consecutive shampooing tests.

The colour of the locks was evaluated in the Munsell system, before and after the test of resistance to shampooing, using a Minolta CM 2002 calorimeter.

According to the Munsell notation, a colour is defined by the expression HV/C in which the three parameters respectively denote the shade or Hue (H), the intensity or Value (V) and the purity or Chromaticity (C), the oblique line in this expression simply being a convention and not indicating a ratio.

The difference between the colour of each lock before and after the test of resistance to shampooing reflects the degradation of the coloration caused by the action of shampooing, and was calculated by applying the Nickerson formula:

$$\Delta E = 0.4 Co \Delta H + 6\Delta V + 3\Delta C,$$

as described, for example, in "Couleur, Industrie et Technique"; pages 14–17; vol. no. 5; 1978, the disclosure of which is specifically incorporated by reference herein.

In this formula, $\Delta E$ represents the difference in colour between two locks, $\Delta H$, $\Delta V$ and $\Delta C$ represent the variation in absolute value of the parameters H, V and C, and Co represents the purity of the lock relative to which it is desired to evaluate the colour difference (purity of the lock before the test).

The results are given in Table II below:

| EXAMPLE | Colour before the test | Colour after the test | Degradation of the colour | | | |
|---|---|---|---|---|---|---|
| | | | $\Delta H$ | $\Delta V$ | $\Delta C$ | $\Delta E$ |
| 1(*) | 0.3 Y 5.8/2.0 | 1.6 Y 6.0/1.8 | 1.3 | 0.2 | 0.2 | 2.8 |
| 2 | 4.2 YR 4.9/2.1 | 4.7 YR 4.9/1.9 | 0.5 | 0 | 0.2 | 1.0 |

(*): example not forming part of the invention

It is seen that the coloration obtained with the dye composition of Example 2 according to the invention, including a para-phenylenediamine derivative of formula (I), is much more resistant to the action of shampooing than the coloration obtained with the dye composition of Example 1, which does not form part of the invention since it contains 2,4,5,6-tetraaminopyrimidine, this compound not corresponding to the definition of the oxidation bases used according to the invention and defined above, but instead corresponding to a compound as described in German patent application DE 2,714,831.

Comparative Examples 3 and 4

The following dye compositions were prepared (contents in grams):

| EXAMPLE | 3(*) | 4 |
|---|---|---|
| Para-phenylenediamine | 0.324 | — |
| 2,6-Dimethyl-para-phenylenediamine dihydrochloride | | 0.627 |
| 2-Amino-3-hydroxypyridine | 0.405 | 0.405 |
| Common dye support | () | () |
| Demineralized water qs | 100 g | 100 g |

It is important to note that the dye compositions of Examples 3 and 4 contain the same molar amount of oxidation base, i.e. $3 \cdot 10^{-3}$ mol.

(*): composition not forming part of the invention
(**): Common dye support:

This was identical to that described for Examples 1 and 2 above.

Each dye composition was mixed, at the time of use, with an equal weight amount of 20-volumes aqueous hydrogen peroxide solution (6% by weight).

Each resulting composition had a pH of about 10 and was applied for 30 minutes to locks of permanent-waved grey hair containing 90% white hairs. The locks of hair were then rinsed, washed with a standard shampoo and then dried.

The locks of hair thus treated were then subjected to a test of resistance to shampooing (Ahiba-Texomat machine), according to the procedure described for Examples 1 and 2 above.

The locks were subjected to 6 consecutive shampooing tests.

The colour of the locks was evaluated in the Munsell system, before and after the test for resistance to shampooing, using a Minolta CM 2002 colorimeter.

The results are given in Table II below:

| EXAMPLE | Colour before the test | Colour after the test | Degradation of the colour | | | |
|---|---|---|---|---|---|---|
| | | | $\Delta H$ | $\Delta V$ | $\Delta C$ | $\Delta E$ |
| 3(*) | 8.85 R 1.3/4.6 | 9.75 R 2.2/4.9 | 0.9 | 0.9 | 0.3 | 8.0 |
| 4 | 8.8 R 1.7/3.8 | 8.7 R 2.0/3.8 | 0.1 | 0.3 | 0 | 2.0 |

(*): example not forming part of the invention

It is seen that the coloration obtained with the dye composition of Example 4 according to the invention, including a para-phenylenediamine derivative of formula (I), is much more resistant to the action of shampoos than the coloration obtained with the dye composition of Example 3 which does not form part of the invention since it contains para-phenylenediamine, this compound not corresponding to formula (I) of the para-phenylenediamine derivatives according to the invention and defined above.

We claim:

1. An oxidation dye composition for dyeing a keratin fiber, comprising, in a medium suitable for dyeing:
   at least one coupler, wherein said at least one coupler is 2-amino-3-hydroxypyridine or an acid addition salt thereof,
   and at least one oxidation base, wherein said at least one oxidation base is
   (a) a paraphenylenediamine selected from the group consisting of:
      2-chloro-paraphenylenediamine,
      2,3-dimethyl-paraphenylenediamine,
      2,6-dimethyl-paraphenylenediamine,
      2,6-diethyl-paraphenylenediamine,
      2,5-dimethyl-paraphenylenediamine, 2-methyl-5-methoxy-paraphenylenediamine,
2,6-dimethyl-5-methoxy-paraphenylenediamine,
N,N-dimethyl-paraphenylenediamine,
N,N-diethyl-paraphenylenediamine,
N,N-dipropyl-paraphenylenediamine,
4-amino-N,N-diethyl-3-methylaniline,
N,N-bis(β-hydroxy-ethyl)-paraphenylenediamine,
4-amino-N,N-bis(β-hydroxyethyl)-3-methylaniline,
4-amino-3-chloro-N,N-bis(β-hydroxyethyl)aniline,
4-amino-N-ethyl-N-carbamylmethylaniline,
4-amino-3-methyl-N-ethyl-N-carbamylmethylaniline,
4-amino-N-ethyl-N-(β-piperidinoethyl)aniline,
4-amino-3-methyl-N-ethyl-N-(β-piperidinoethyl)aniline,
4-amino-N-ethyl-N-(β-morpholinoethyl)-aniline,
4-amino-3-methyl-N-ethyl-N-(β-morpholinoethyl)aniline,
4-amino-N-ethyl-N-(β-acetylaminoethyl)aniline,
4-amino-N-(β-methoxyethyl)aniline,
4-amino-3-methyl-N-ethyl-N-(β-acetylaminoethyl)aniline.
4-amino-N-ethyl-N-(β-mesylaminoethyl)aniline,
4-amino-3-methyl-N-ethyl-N-(β-mesylaminoethyl)aniline,
4-amino-N-ethyl-N-(β-sulphoethyl)aniline,
4-amino-3-methyl-N-ethyl-N-(β-sulphoethyl)aniline,
N-[4'-(amino)phenyl]morpholine,
N-[4'-(amino)phenyl]piperidine,
2-β-hydroxyethyl-paraphenylenediamine,
2-fluoro-paraphenylenediamine,
2-carboxy-paraphenylenediamine,
2-sulpho-paraphenylenediamine,
2-isopropyl-paraphenylenediamine,
N-(β-hydroxypropyl)-paraphenylenediamine,
2-hydroxymethyl-paraphenylenediamine,
N,N-dimethyl-3-methyl-paraphenylenediamine,
N-ethyl-N-(β-hydroxyethyl)-paraphenylenediamine,
N-(β-γ-dihydroxypropyl)-paraphenylenediamine,
2-β-hydroxyethyloxy-paraphenylenediamine, and acid addition salts thereof, or
(b) a para-aminophenol or an acid addition salt thereof.

2. An oxidation dye composition according to claim 1, wherein said keratin fiber is human hair.

3. An oxidation dye composition according to claim 1, wherein said $C_1$–$C_4$ alkyl and $C_1$–$C_4$ alkoxy of formula (I) are methyl, ethyl, propyl, methyloxy or ethyloxy radicals.

4. An oxidation dye composition according to claim 1, wherein said para-aminophenols is a compound of formula (II) or an acid addition salt thereof:

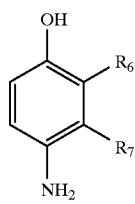

(II)

wherein:
$R_6$ is hydrogen, $C_1$–$C_4$ alkyl, $C_1$–$C_4$ monohydroxyalkyl, $(C_1$–$C_4)$alkoxy$(C_1$–$C_4)$alkyl, $C_1$–$C_4$ aminoalkyl, or hydroxy$(C_1$–$C_4)$alkylamino$(C_1$–$C_4)$alkyl;
$R_7$ is hydrogen, fluorine, $C_1$–$C_4$ alkyl, $C_1$–$C_4$ monohydroxyalkyl, $C_2$–$C_4$ polyhydroxyalkyl, $C_1$–$C_4$ aminoalkyl, cyano$(C_1$–$C_4)$alkyl, or $(C_1$–$C_4)$alkoxy$(C_1$–$C_4)$alkyl;
and further wherein at least one of the radicals $R_6$ and $R_7$ represents a hydrogen atom.

5. An oxidation dye composition according to claim 4, wherein said para-aminophenols is para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, or an acid addition salt thereof.

6. An oxidation dye composition according to claim 1, wherein said acid addition salts are hydrochlorides, hydrobromides, sulphates or tartrates.

7. An oxidation dye composition according to claim 1, wherein said at least one coupler is present in a concentration ranging from approximately 0.0001 to 5% by weight relative to the total weight of said oxidation dye composition.

8. An oxidation dye composition according to claim 7, wherein said at least one coupler is present in a concentration ranging from approximately 0.005 to 3% by weight relative to the total weight of said oxidation dye composition.

9. An oxidation dye composition according to claim 1, wherein said at least one oxidation base is present in a concentration ranging from approximately 0.0005 to 12% by weight relative to the total weight of said oxidation dye composition.

10. An oxidation dye composition according to claim 9, wherein said at least one oxidation base is present in a concentration ranging from approximately 0.005 to 6% by weight relative to the total weight of said oxidation dye composition.

11. An oxidation dye composition according to claim 1, wherein said medium suitable for dyeing is water or a mixture of water and at least one organic solvent.

12. An oxidation dye composition according to claim 11, wherein said at least one organic solvent is $C_1$–$C_4$ lower alkanols, glycerol, glycols, glycol ethers, or aromatic alcohols.

13. An oxidation dye composition according to claim 12, wherein said at least one organic solvent is present in a concentration ranging from approximately 1 to 40% by weight relative to the total weight of said oxidation dye composition.

14. An oxidation dye composition according to claim 13, wherein said at least one organic solvent is present in a concentration ranging from approximately 5 to 30% by weight relative to the total weight of said oxidation dye composition.

15. An oxidation dye composition according to claim 1, wherein said oxidation dye composition has a pH ranging approximately from 3 to 12.

16. An oxidation dye composition according to claim 15, wherein said oxidation dye composition has a pH ranging approximately from 5 to 11.

17. An oxidation dye composition according to claim 1, wherein said oxidation dye composition is in the form of a liquid, cream, or gel.

18. A process for dyeing keratin fiber comprising the steps of:
applying at least one dye composition according to claim 1 to said keratin fiber; and
developing the colour of said at least one dye composition at acidic, neutral or alkaline pH by an oxidizing agent, wherein said oxidizing agent is either added to the dye composition just prior to said applying step or said oxidizing agent is present in an oxidizing composition separately applied simultaneously with or sequentially to said at least one dye composition.

19. A process for dyeing keratin fibers according to claim 18, wherein said keratin fiber is human hair.

20. A process according to claim 18, wherein said oxidizing agent is hydrogen peroxide, urea peroxide, an alkali metal bromate or a persalt.

21. A process according to claim 20, wherein said persalt is a perborate or persulphate.

22. A process according to claim 20, wherein said oxidizing agent is hydrogen peroxide.

23. A multi-compartment device comprising a first compartment including an oxidation dye composition according to claim 1 and a second compartment including an oxidizing composition.

* * * * *

UNITED STATES PATENT AND TRADEMARK OFFICE
CERTIFICATE OF CORRECTION

PATENT NO.: 5,900,028

DATED: May 4, 1999

INVENTOR(S): Marie-Pascale AUDOUSSET

It is certified that an error appears in the above-identified patent and that said Letters Patent is hereby corrected as shown below:

Claim 1, col. 9, line 9, change "am ino" to --amino--.

Signed and Sealed this

Seventh Day of September, 1999

Attest:

Q. TODD DICKINSON

*Attesting Officer*   Acting Commissioner of Patents and Trademarks